US00PP25665P2

(12) United States Plant Patent
Stemkens

(10) Patent No.: US PP25,665 P2
(45) Date of Patent: Jun. 30, 2015

(54) ***VERBENA* PLANT NAMED 'VEAZ0016'**

(50) Latin Name: *Verbena hybrida*
Varietal Denomination: VEAZ0016

(71) Applicant: Syngenta Crop Protection AG, Basel (CH)

(72) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 93 days.

(21) Appl. No.: 13/998,050

(22) Filed: Sep. 26, 2013

(51) Int. Cl.
*A01H 5/02* (2006.01)

(52) U.S. Cl.
USPC ..... Plt./308

(58) Field of Classification Search
USPC ..... Plt./308
CPC ..... A01H 5/02; A01H 5/00
See application file for complete search history.

*Primary Examiner* — Kent L Bell
(74) *Attorney, Agent, or Firm* — Joshua L. Price

(57) ABSTRACT

A new *Verbena* plant named 'VEAZ0016' particularly distinguished by the large sized umbel and flowers, bold red colored flowers with a white-eye, is early to flower with good floriferousness on plants of medium vigor and medium green foliage.

1 Drawing Sheet

Latin name of the genus and species of the plant claimed: *Verbena hybrida.*

Varietal denomination: 'VEAZ0016'.

BACKGROUND OF THE NEW PLANT

The present invention comprises a new *Verbena*, botanically known as *Verbena hybrida*, and hereinafter referred to by the variety name 'VEAZ0016'.

'VEAZ0016' is a product of a planned breeding program. The new cultivar has large sized umbel and flowers, bold red colored flowers with a white-eye, is early to flower with good floriferousness on plants of medium vigor and medium green foliage.

'VEAZ0016' originated from a hybridization made in August 2007 in a greenhouse environment in Enkhuzien, The Netherlands. The female parent was the proprietary plant designated 'HO641-7', unpatented, with smaller solid red flower color and a plant habit with fewer branches than 'VEAZ0016'.

The male parent of 'VEAZ0016' was an unpatented hybrid seedling identified as 'HO513-1' with pink flower color with a smaller eye and is later to flowers than 'VEAZ0016'. The seed was sown in February 2008 in in a greenhouse environment in Enkuizen, the Netherlands.

'VEAZ0016' was selected as one flowering plant within the progeny of the stated cross in August 2008 in a greenhouse environment in Enkhuzien, The Netherlands.

The first act of asexual reproduction of 'VEAZ0016' was accomplished when vegetative cuttings were propagated from the initial selection in August 2008 in a greenhouse environment in Enkhuzien, The Netherlands.

BRIEF SUMMARY OF INVENTION

Horticultural examination of plants grown from cuttings of the plant initiated in August 2008 in Enkhuzien, The Netherlands, and continuing thereafter, has demonstrated that the combination of characteristics as herein disclosed for 'VEAZ0016' are firmly fixed and are retained through successive generations of asexual reproduction.

'VEAZ0016' has not been observed under all possible environmental conditions. The phenotype may vary significantly with variations in environment such as temperature, light intensity, and day length.

Plant Breeder's Rights for this cultivar were applied for in Canada on Nov. 9, 2012, No. 12-7791 and at the Community Plant Variety Office on Sep. 25, 2012, No. 2012-2027. 'VEAZ0016' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawing shows typical flower and foliage characteristics of 'VEAZ0016' with colors being as true as possible with an illustration of this type.

Figure 1:
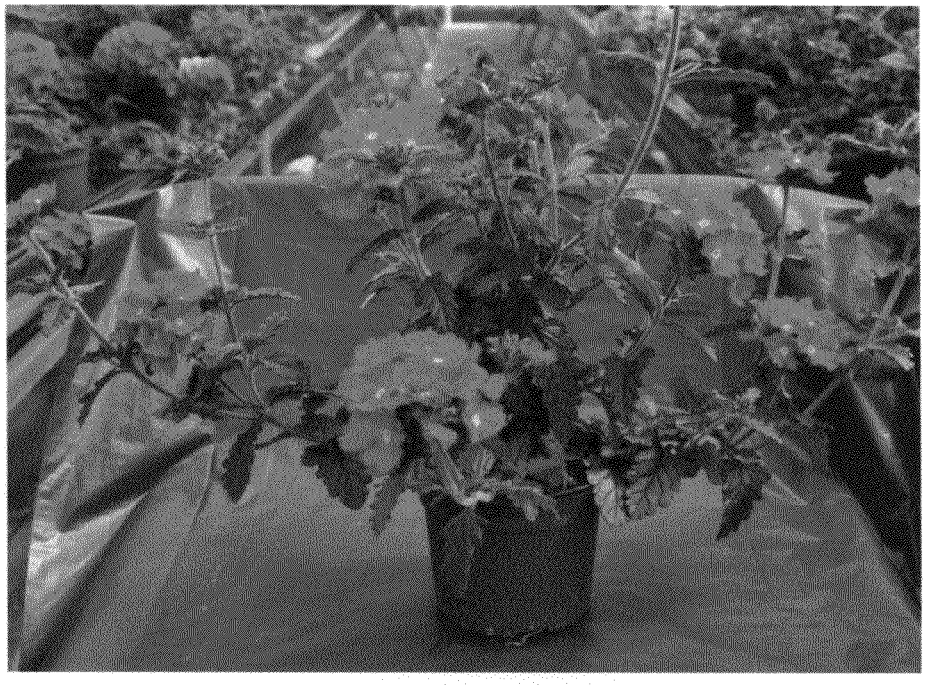
Figure 2:
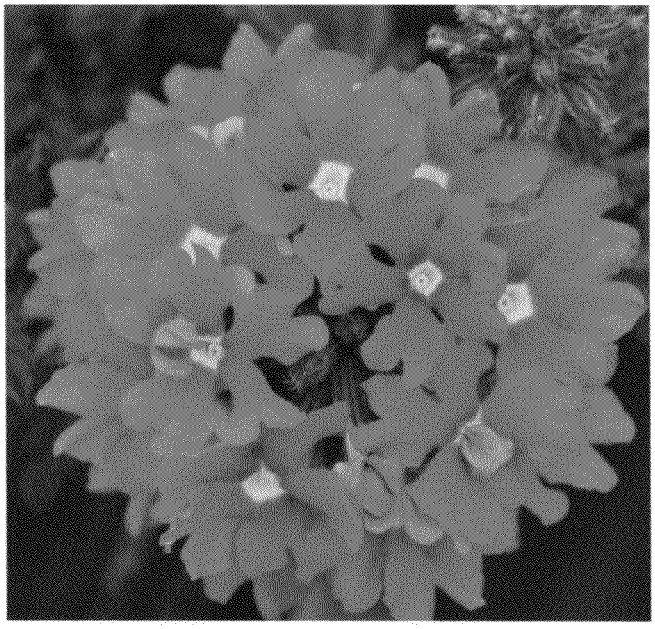

The photographic drawing shows in FIG. 1 a flowering plant of the new variety and in FIG. 2 a close-up of the inflorescences.

DETAILED BOTANICAL DESCRIPTION

The plant descriptions and measurements were taken in Enkhuzien, The Netherlands in August from plants growing in an outdoors trial in one (1) meter window boxes with each box containing 5 plants. The plants used were about 5 months old.

The aforementioned photographs were taken in Andijk, The Netherlands in May from plants growing in a greenhouse trial in 12 cm pots. These plants used were about 11-12 weeks old with no terminal pinches to the plant.

Color references are made to The Royal Horticultural Society Colour Chart (R.H.S.) 2001.

TABLE 1

DIFFERENCES BETWEEN THE NEW VARIETY 'VEAZ0016' AND A MOST SIMILAR VARIETY

| | 'VEAZ0016' | 'SCY' (U.S. Pat. No. PP21,081) |
|---|---|---|
| Flower color: | Scarlet with white eye | More red with white eye |
| Flower size: | Larger | Smaller |
| Umbel size: | Larger | Smaller |

Plant:

*Form, growth and habit*.—Herbaceous; mounding and outwardly spreading growth habit; medium vigor.

*Plant height*.—18-22.0 cm.

*Plant height* (*inflorescence included*).—28-30.0 cm.

*Plant width*.—30-40.0 cm.

Roots:

*Number of days to initiate and produce roots*.—10-14 days at about 22 degrees C.

*Type*.—Fine, fibrous, free branching.

*Color*.—RHS N155B but whiter.

Foliage:

*Arrangement*.—Alternate, simple.

*Immature, leaf color, upper surface*.—Closest to RHS 143A to RHS 143B.

*Immature, leaf color, lower surface*.—Somewhat duller than RHS 143C.

*Mature, leaf color, upper surface*.—Closest to RHS 137C.

*Mature, leaf color, lower surface*.—Closest to RHS 138A.

*Length*.—3.0-4.5 cm.

*Width*.—1.8-2.1 cm.

*Shape*.—Narrowly elliptic.

*Base shape*.—Attenuate.

*Apex shape*.—Acute.

*Margin*.—Dentate.

*Texture, upper surface*.—Pilose.

*Texture, lower surface*.—Pilose, with glandular hairs mostly on the mid-veins.

*Color of veins, upper surface*.—RHS 144C.

*Color of veins, lower surface*.—RHS 145B.

*Pattern of veining*.—Pinnate.

*Petiole color, upper side*.—RHS 144C.

*Petiole color, lower side*.—RHS 145B.

*Petiole length*.—0.3-0.5 cm.

*Petiole width*.—0.3 cm.

*Texture*.—Heavily pilose.

Stem:

*Quantity of main branches per plant*.—About 10-15.

*Color of stem*.—RHS 143C with weak anthocyanins sometimes at the upper portions of about RHS 199B.

*Stem length*.—About 20-27.0 cm.

*Stem width*.—0.3-3.5 cm.

*Length of internodes*.—3.5-6.0 cm.

*Texture*.—Hirtellous, glandular hairs.

*Color of peduncle*.—RHS 143B.

*Length of peduncle*.—1.5-4.0 cm.

*Peduncle diameter*.—0.2-0.25 cm.

*Texture*.—Pilose, glandular hairs.

Inflorescence:

*Type*.—Terminal, umbel-like, but actually a spike, umbrella-shaped to semi spherical.

*Blooming habit*.—Flowers continuously in summer months.

*Lastingness of individual blooms on the plant*.—About 6 days in the greenhouse and depending on cultural and environmental conditions.

*Fragrance*.—None.

*Number of inflorescences per plant*.—15-20 with open flowers and with additional in immature stages.

*Horizontal diameter of inflorescence*.—5.5-6.0 cm.

*Depth of inflorescence*.—About 2.5 cm.

*Number of florets per inflorescence* (*including any buds at the time*).—About 20-25.

Bud (just when opening/showing color):

*Color*.—RHS 46A.

*Length*.—1.5 cm.

*Width*.—0.3 cm.

*Shape*.—Tubular with bulbous end.

Corolla:

*Form*.—Sessile; salverform, composed of 5 partly fused petals with a base of a narrow tube.

*Immature color, upper surface*.—RHS 45B.

*Immature color, lower surface*.—RHS 46B.

*Mature color, upper surface*.—Between RHS 44A and RHS 45B with RHS 150D 'eye'.

*Mature color, lower surface*.—RHS 46C with RHS 155C but white 'eye'.

*Floret diameter*.—About 2.2 cm.

*Floret length* (*depth*).—About 2.3 cm.

*Petal length*.—0.9-1.0 cm.

*Petal width*.—0.7-0.9 cm.

*Shape*.—Obovate.

*Apex shape*.—Most retuse, some more rounded.

*Margin*.—Entire.

*Petal texture, upper surface*.—Papillose.

*Petal texture, lower surface*.—Papillose.

*Corolla tube color inside*.—Weakly RHS 56D.

*Corolla tube color outside*.—RHS 145B near the corolla, and RHS 145D near the base.

*Corolla tube length*.—1.7-1.8 cm.

*Corolla tube width*.—0.2 cm.

*Corolla texture, inside*.—Papillose with hairs at corolla flare.

*Corolla texture, outside*.—Papillose.

*Throat hair color*.—RHS 56D.

Calyx:

*Type*.—Five sepals whose margins are fused to each other along their length, with a transparent membrane of less than 0.1 cm in width and with one smaller sepal attached to the base of the calyx.

*Color of sepals*.—RHS 143A.

*Length of sepals*.—1.1 cm.

*Width of sepals*.—0.2 cm.

*Sepal shape*.—Linear.

*Apex shape*.—Acute.

*Margins*.—Entire where not fused.

*Texture, upper surface*.—Glabrous.

*Texture, lower surface*.—Pilose, glandular hairs.

Reproductive organs:

Gynoecium.—Pistil: 1. Pistil length: 2.0-2.3 cm. Style color: RHS 144D. Style length: 1.6-2.0 cm. Stigma color: RHS 144C. Stigma shape: Bi-parted. Ovary color: RHS 144D. Ovary length: 0.2 cm. Ovary width: 0.15 cm.

*Androecium*.—Stamens: Anthers and filaments fused to upper half of corolla tube; four anthers with two pollen sacs per anther. Color of filaments: RHS 149D with slight hint of RHS 56D under the anthers. Filament length: 0.2-0.3 cm. Anther color: RHS 144D. Anther length: 0.1 cm. Color of pollen: RHS 154D. Pollen amount: Good.

Fertility/seed set: Has not been determined to date.

Disease/pest resistance: Has not been determined to date.

What is claimed is:

1. A new and distinct variety of *Verbena* plant named 'VEAZ0016' substantially as illustrated and described herein.

* * * * *